(12) United States Patent
Hall et al.

(10) Patent No.: US 7,048,541 B2
(45) Date of Patent: May 23, 2006

(54) IMPLANT HAVING ATTACHMENT AND HOLE-INSERT PARTS, AND METHOD FOR PRODUCING SUCH AN IMPLANT

(75) Inventors: Jan Hall, Gothenburg (SE); Fredrik Engman, Molnlycke (SE)

(73) Assignee: Nobel Biocare AB, (SE)

( * ) Notice: Subject to any disclaimer, the term of this patent is extended or adjusted under 35 U.S.C. 154(b) by 169 days.

(21) Appl. No.: 10/240,548

(22) PCT Filed: Apr. 3, 2001

(86) PCT No.: PCT/SE01/00727

§ 371 (c)(1),
(2), (4) Date: Apr. 22, 2003

(87) PCT Pub. No.: WO01/74412

PCT Pub. Date: Oct. 11, 2001

(65) Prior Publication Data
US 2003/0157460 A1    Aug. 21, 2003

(30) Foreign Application Priority Data
Apr. 4, 2000    (SE) .................................. 0001201

(51) Int. Cl.
*A61C 8/00*    (2006.01)
(52) U.S. Cl. .................................. 433/201.1; 433/173
(58) Field of Classification Search ............. 433/201.1, 433/172–176; 623/16.11, 23.5, 23.53, 23.55
See application file for complete search history.

(56) References Cited

U.S. PATENT DOCUMENTS

| | | | |
|---|---|---|---|
| 4,052,754 A | 10/1977 | Homsy | |
| 4,179,485 A | 12/1979 | Tritten | |
| 4,463,753 A | 8/1984 | Gustilo | |
| 4,542,539 A | 9/1985 | Rowe et al. | |
| 4,564,429 A | 1/1986 | Depiereux | |
| 4,713,076 A | 12/1987 | Draenert | |
| 4,801,300 A * | 1/1989 | Kurze et al. | ............. 623/23.36 |
| 4,878,919 A | 11/1989 | Pavlansky et al. | |
| 4,959,054 A | 9/1990 | Heimke et al. | |
| 5,002,488 A | 3/1991 | Homsy | |
| 5,084,050 A | 1/1992 | Draenert | |

(Continued)

OTHER PUBLICATIONS

Abstract only of BR 8905067 A, Apr. 1991, Baumer, Brazil.*

*Primary Examiner*—John J Wilson
(74) *Attorney, Agent, or Firm*—Connolly, Bove, Lodge & Hutz LLP

(57) ABSTRACT

An implant (1) has attachment and hole-insert parts (2, 3) with an outer surface or outer surfaces having external layer arrangements (6, 7). The implant can be provided in a known manner with threads (3a, 3b) on cylindrical and conical portions. The implant is made in principle in two production stages. In a first production stage, the outer surface or outer surfaces (6a) of the implant are given a relatively high roughness value and/or a relatively high degree of porosity. In a second stage, the uneven or porous surface thus obtained is coated with an oxide layer (7) which can be uniform or can have different thicknesses along the longitudinal and/or circumferential directions(s) of the implant. In one embodiment, the oxide layer (7) can be coated with a bone-growth agent or bone-growth-promoting agent and/or calcium phosphate (16), for example by means of chemical deposition, dipping or sputtering.

17 Claims, 2 Drawing Sheets

U.S. PATENT DOCUMENTS

Figure 1:
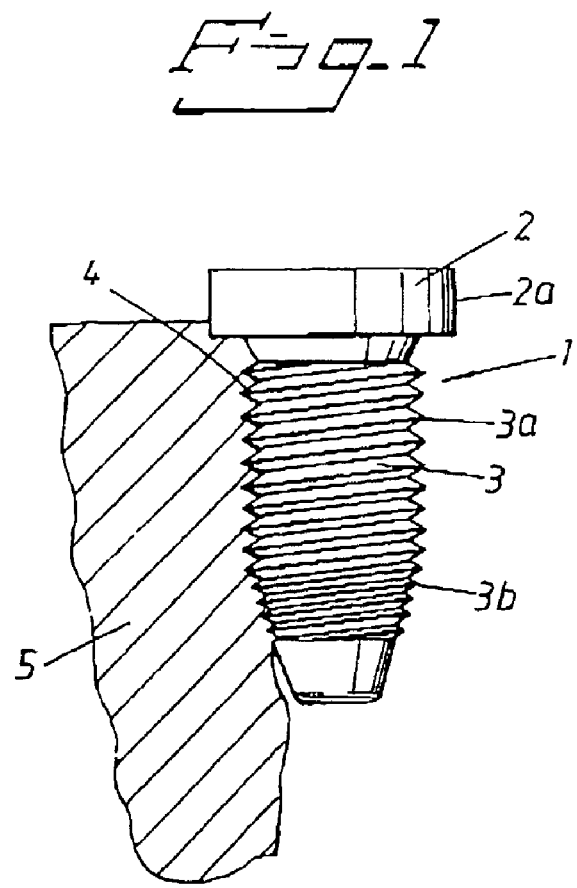

| | | |
|---|---|---|
| 5,176,712 A | 1/1993 | Homsy |
| 5,181,850 A * | 1/1993 | Neumeyer ................. 433/205 |
| 5,211,833 A * | 5/1993 | Shirkhanzadeh ............ 205/322 |
| 5,360,448 A | 11/1994 | Thramann |
| 5,464,440 A | 11/1995 | Johansson |
| 5,478,237 A * | 12/1995 | Ishizawa ................. 433/201.1 |
| 5,489,306 A | 2/1996 | Gorski |
| 5,736,152 A | 4/1998 | Dunn |
| 5,871,486 A | 2/1999 | Huebner et al. |
| 5,885,079 A | 3/1999 | Niznick |
| 5,989,027 A | 11/1999 | Wagner et al. |
| 6,027,742 A | 2/2000 | Lee et al. |
| 6,301,418 B1 | 10/2001 | Freier et al. |
| 6,379,153 B1 | 4/2002 | Schroering |
| 6,689,170 B1 * | 2/2004 | Larsson et al. .......... 623/23.53 |

* cited by examiner

IMPLANT HAVING ATTACHMENT AND HOLE-INSERT PARTS, AND METHOD FOR PRODUCING SUCH AN IMPLANT

The present invention relates to an implant having attachment and hole-insert parts provided with one or more outer surfaces having one or more layer arrangements. The invention also relates to a method for producing external layer arrangements on one or more outer surfaces of an implant with attachment and hole-insert parts.

There are a great many implants of this type. Reference may be made, for example, to the implant according to WO 97/43976 from the same applicant as the present invention. Reference may also be made, for example, to the implant according to WO 97/03621. Reference may also be made to the Swedish patent applications from the same applicant as the present application, bearing numbers 9901971-3, 9901973-9 and 9901974-7. Reference may also be made to U.S. Pat. Nos. 5,571,017, 5,842,85, 5,885,079, 5,947,735 and 5,989,027.

A characteristic feature of an implant can be that it has an attachment part which is intended to extend up through the jaw bone to permit connection, via a spacer element, of a superstructure for the implant. In the case of what is known as a self-tapping implant, the latter is provided with one or more outer threads which can have a cylinder shape or cone shape. From some of the above reference documents, it is also known to produce implants with surfaces of different roughness values and/or porosities.

In the type of implant in question, there is a need to be able to offer a wide range of implants based on the same manufacturing technique. In some cases it may be of advantage to use outwardly porous surfaces or surface areas where the porosity has to satisfy different screwing procedures with different bone density of the jaw bone or tooth bone in question. In soft jaw bone, it may be desirable to use a coarser porosity, whereas in hard bone structures in the jaw and tooth bone it may be advantageous to use lower degrees of porosity or to use precision-worked or precision-machined surfaces which offer less resistance during screwing. In some cases it may also be advantageous to insert a barrier in order to prevent so-called ion release. In dentistry it is advantageous in some cases to be able to provide porosities of different degrees in order to increase the surface areas for bone union. In other cases it is important to reduce the roughness value/porosity of said surfaces. In cases where the porosities are used as depots for bone-growth agents or bone-growth promoting agents, it is expedient to be able to offer depots of greater or lesser extent or smooth surfaces on which, for example, calcium phosphate is to be applied. It is an object of the invention to solve the problems mentioned above.

It is preferable for the proposed solutions to be able to follow accepted and well-proven methods to establish a choice of porosities, smooth surfaces, coatings, etc. The invention solves this problem too.

That which can principally be regarded as characterizing an implant according to the invention is that one or more arrangements have a machined or treated surface with a high roughness value and/or porosity and an outer oxide layer applied on top of this surface.

In one embodiment of the inventive concept, the oxide layer has a thickness in the range of from 5 nm to 20 μm. The oxide layer can in this case have a thickness varying along the longitudinal and/or circumferential direction(s) of the implant. In one embodiment, a layer of calcium phosphate can be applied on top of the oxide layer.

A method according to the invention is characterized in that the implant is machined and/or treated to produce a high roughness value or a preferably high porosity on the surface or surfaces, and in that said surface or surfaces are thereafter coated with an oxide layer. The oxide layer can be obtained with the aid of electrochemical treatment in which the surface or surfaces of the implant are dipped in an electrolyte, in which an anode and cathode arrangement is provided. To establish said porosity, a voltage is applied to the anode and cathode arrangement, and a current produced by the voltage is led via the electrolyte and the implant dipped in the latter. With this method, a high porosity can be obtained if the voltage assumes a relatively high value, for example a value of 300 volts or more, and a certain type of electrolyte is used. In a possible second stage, the oxide layer can be applied in a similar manner, the implant being dipped in the same electrolyte or in another electrolyte, and the voltage value being chosen at a lower level so that the oxide layer is established with a lower degree of porosity or a porosity which is almost zero. Such a smoother oxide layer can also be produced by heat treatment of the implant in an oxygen-containing atmosphere.

Further developments of said implant and method are set out in the attached subclaims concerning the implant and the method, respectively.

The method proposed above makes it possible to produce a range of implants with different porosities, porosity extents, treated surfaces, etc. From this range it is possible to choose the implant which is best suited for the treatment situation in question. The quality of the bone in question, for example jaw bone or tooth bone, varies greatly in the same individual and between different individuals. The bone structure of the upper jaw is relatively soft, whereas the bone structure of the lower jaw can vary from a relatively soft structure to a hard structure at the front of the jaw. Implants of greater or lesser porosity can thus be produced and, similarly, oxide layers with a fine surface structure can be applied on top of the already existing surface with a high roughness value or porosity. Ion release can be limited in this way, and the smoother surface can also constitute a substrate surface for layers having bone-growth agents or bone-growth-promoting agents. The oxide layer applied on top of the uneven or porous surface can consist of a thin or relatively thick oxide layer which can be applied in a known manner by simple dipping in a voltage-connected electrolyte in a manner known per se. The form and thickness of the oxide layer can be varied. Thus, for example, the oxide layer can have a greater thickness at the central or outer parts of the implant. The oxide layer can be applied here and there on the porous outer surface in question. Alternatively, the oxide layer can be varied in thickness in the circumferential direction of the implant, and so on.

Figure 2:
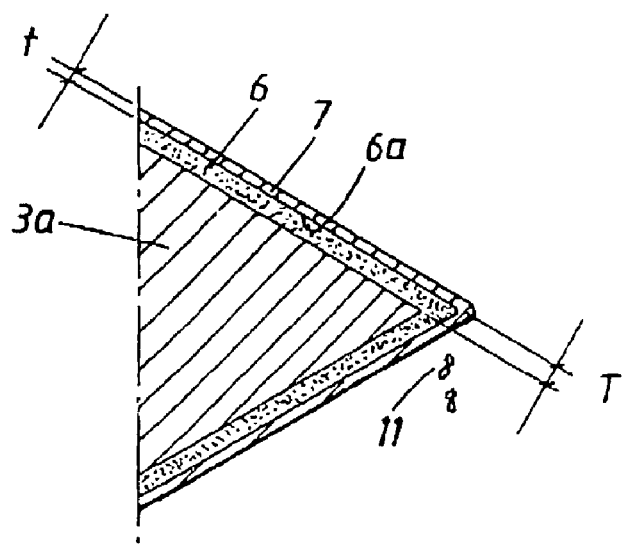
Figure 3:
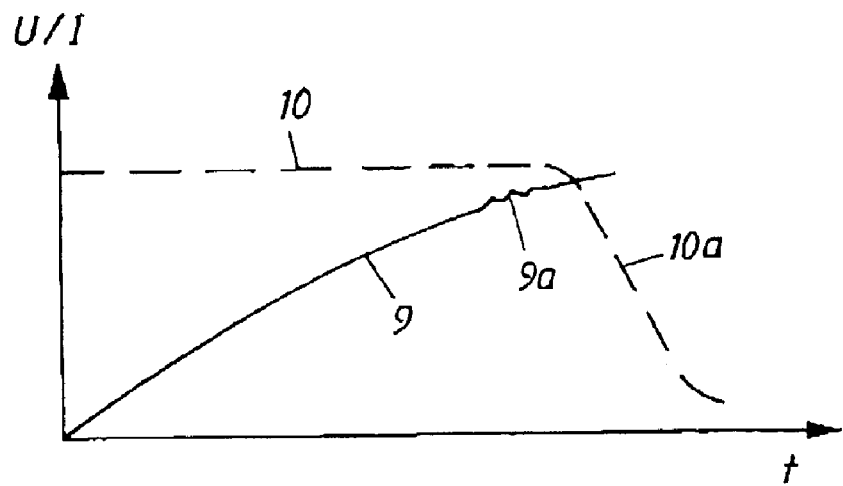
Figure 4:
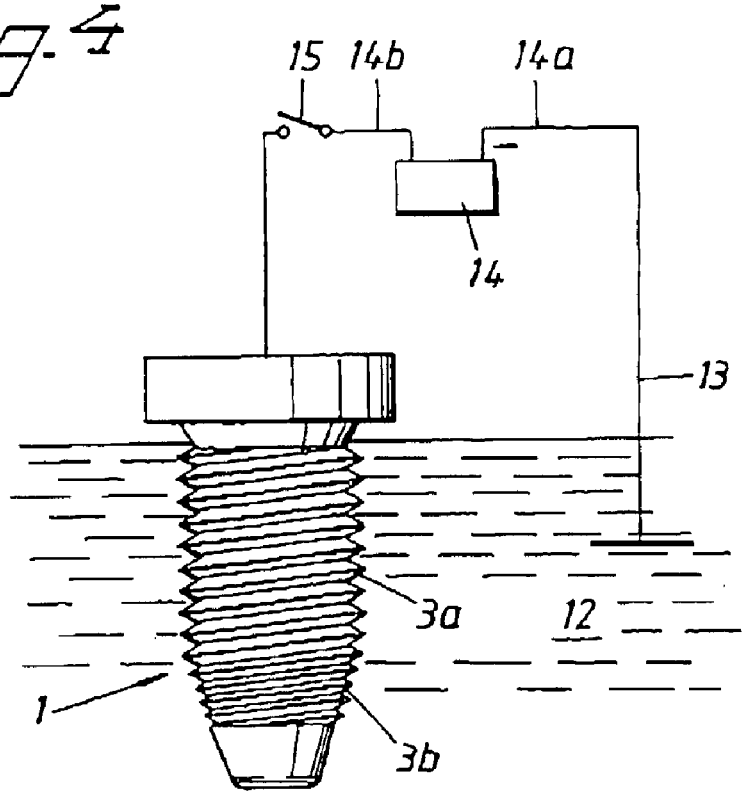

A presently proposed embodiment of an implant and of a method according to the invention will be described below with reference to the attached drawings, in which:

FIG. 1 is a vertical section showing an implant applied in a partly shown tooth or jaw bone, FIG. 2 is an enlarged longitudinal section showing the outer part of a thread on the implant according to FIG. 1, from which it will be seen that the outer surface of the thread has been provided with layers according to the invention, FIG. 3 is a diagram showing voltages and currents which arise in an electrochemical method on an implant dipped in an electrolyte, and FIG. 4 is a vertical section and schematic representation showing the implant according to FIG. 1 dipped in an electrolyte, and an anode and cathode arrangement provided in the latter.

An implant of the type specified above is indicated by 1 in FIG. 1, i.e. an implant which can be found in the prior art and is described inter alia in the documents referred to above. The implant has an attachment part 2, for example for a spacer element, and a hole-insert part 3. The outer surface 2a of the attachment part can be smooth or precision-worked (for example machined) or can have a greater or lesser porosity. At the top, the hole-insert part 3 can have a cylindrical portion with outer thread 3a, and a conical portion with outer thread 3b at the free/lower end of the implant. The implant is of the so-called self-tapping type and can be screwed into a hole 4 in a bone, for example a tooth bone or jaw bone. In the present case, the surface layer of the threaded portions has a relatively high roughness value/porosity created, for example, by etching or shot-peening which are known per se. In accordance with the invention, an oxide layer as described below is applied on the outside of said relatively rough and porous layers.

In FIG. 2, the layer with the high roughness value is indicated by 6 and the outer oxide layer is indicated by 7. As has already been mentioned, the layer 6 can be created by etching or shot-peening of the implant part in question. The layer 6 can have a surface roughness of between 0.4 and 5 μm. The thickness t of the outer oxide layer 7 assumes values preferably in the range of from 4–5 nm to ca. 20 μm. The layer can be very porous with $1 \times 10^7$-$1 \times 10^{10}$ pores/cm². In a preferred embodiment, the porosity is considerably lower in the outer oxide layer 7.

Methods which are known per se can be used for applying said layer 7. In the present case, the electrochemical method is preferably used which is described in the abovementioned Swedish patent applications 9901971-3 and 9901974-7. A voltage/current ratio in accordance with the figure occurs in such an electrochemical method. As this method is already known per se, it will not be described here, but reference may be made to said Swedish patent applications. As can be seen from FIG. 3, a voltage rise takes place according to curve 9, and a current 10 has at the outset a substantially constant value and after a time drops in accordance with curve part 10a. The formation of the titanium oxide layer and its final properties and structures are determined by a number of parameters in said process. Thus, the composition of the electrolyte and its temperature, the applied voltage and current, the electrode geometry and the treatment time, etc., affect the thickness, degree of porosity, etc., in the titanium oxide layer to be created. Oxide thicknesses and porosities can thus be varied with the aid of said parameters. For example, when the layer 7 has a substantial thickness according to FIG. 2, a relatively high voltage, for example a voltage of 300 volts, will be used. A constant current (of curve part 10) is of the order of magnitude of 0.2 ampere. It has been found that as the voltage rises towards said order of magnitude, a certain spark formation occurs at the electrolyte surface and between the electrolyte and the outer surface part in question. This spark formation can be used to eliminate burrs which arise during machining of the inner surface 8 of the implant. This removal of burrs is symbolized by 11 in FIG. 2.

FIG. 4 shows those parts of the implant which are to be provided with the oxide layer 7 being dipped in an electrolyte 12 in accordance with the abovementioned known electrochemical method. In this case, the implant functions principally as an anode in a combined anode and cathode arrangement in which the cathode part has been symbolized by 13. An energy source is indicated by 14 and the negative potential 14a of the energy source is connected to the cathode 13 and the positive potential 14b is connected to the anode/implant. The connection can be effected by way of a connection member 15, by means of which the positive potential 14 is connected to the anode/implant.

As regards the application of the layer 7, reference is also made to application XXXX which was filed on the same day and which relates to formation of implants with extended zones in which the porosity decreases continuously within each zone. For production of the underlying surface layer 6, the implant, for example of titanium, is provided with an outer surface 6a with a preferably high roughness value which has been established by means of shot-peening, etching, plasma spraying, etc. In the electrochemical method, the layer 7 is then produced with suitable adjustment of said parameters.

By means of what has been proposed above, different types of implants which are based on the same technology can be produced. The structures and thicknesses of the layers 6 and 7 can be determined according to the respective dental situation and the purpose of the implant is to achieve the optimum result. The outer layers 6 or 7 can have uniform thicknesses around the whole circumference of the respective outer surface. Alternatively, they can extend along only parts of the circumference. In a further alternative, the layer 6 can extend along all or part of the circumference and can be covered only partially by the outer layer. This also applies to the extents in the longitudinal or height direction. According to FIG. 2, the outer oxide layer can be provided on its outer surface 7a with a coating of calcium phosphate 16 which is sputtered or otherwise applied to said outer surface 7a once the outer layer 7 has been applied.

The invention is not limited to the embodiment described above by way of example, and instead it can be modified within the scope of the attached patent claims and the inventive concept.

The invention claimed is:

1. A titanium implant comprising attachment and hole-insert parts including at least one outer surface having external layer arrangements, wherein:
   at least one layer arrangement among said layer arrangements has a machined or treated inner surface and an outer titanium oxide layer applied on top of said inner surface;
   said inner surface has a high roughness value and/or porosity; and
   said outer titanium oxide layer has a thickness in the range of 5 nm to 20 μm and a roughness value which is lower than the roughness value of said inner surface.

2. A titanium implant according to claim 1, wherein the thickness of said outer titanium oxide layer varies along a longitudinal and/or circumferential direction of the implant.

3. A titanium implant according to claim 2, wherein the at least one external layer arrangement comprises at least one of to following applied on top of the titanium oxide layer: a bone-growth agent, a bone-growth-promoting agent and a coating of calcium phosphate.

4. A titanium implant according to claim 2, wherein the implant comprises one or more outer threads on said hole-insert parts.

5. A titanium implant according to claim 1, wherein said at least one layer arrangement comprises at least one of the following applied on top of the titanium oxide layer: a bone-growth agent, a bone-growth-promoting agent and a coating of calcium phosphate.

6. A titanium implant according to claim 5, wherein the implant comprises one or more outer threads on said hole-insert parts.

7. A titanium implant according to claim 1, wherein the implant comprises one or more outer threads on said hole-insert parts.

8. A titanium implant according to claim 1, wherein the at least one external layer arrangement comprises at least one of the following applied on top of the titanium oxide layer: a bone-growth agent, a bone-growth-promoting agent and a coating of calcium phosphate.

9. A titanium implant according to claim 1, wherein the implant comprises one or more outer threads on said hole-insert parts.

10. A method for producing at least one external layer arrangement on at least one outer surface of a titanium implant having attachment and hole-insert parts, comprising:
   machining and/or treating said at least one outer surface to produce at least one machined and/or treated surface having a high roughness value and/or a high degree of porosity;
   subsequently coating said at least one machined and/or treated surface with a titanium oxide layer having a thickness in the range of 5 nm to 20 µm and a roughness value which is lower than the roughness value of said at least one machined and/or treated surface.

11. A method according to claim 10, wherein a structure of the at least one external layer arrangement is obtained with the aid of electrochemical treatment in which the at least one machined and/or treated surface is obtained by means of eletrolyte and an anode and cathode arrangement to which the implant is applied, and wherein the anode and cathode arrangement is connected to a voltage so that a current passes through the implant.

12. A method according to claim 11, wherein the burr-eliminating effect is obtained at a thread or threads of the implant.

13. A method according to claim 11, wherein, to establish said porosity, the chosen voltage is high, and the current thereby obtained causes spark formation at a transition between the electrolyte and the implant, and wherein, upon said spark formation, a burr-eliminating effect is obtained on said at least one outer surface.

14. A method according to claim 10, wherein the implant is dipped in an electrolyte and current is led via electrolyte-coated parts of the implant.

15. A method according to claim 10, wherein said at least one outer surface is machined by means of blasting.

16. A method according to claim 10, wherein at least one of the following is applied on top of the titanium oxide layer by wet chemical deposition or sputtering: a bone-growth agent, a bone-growth-promoting agent and calcium phosphate.

17. A method according to claim 10, wherein a bone-growth agent or bone-growth-promoting agent is applied on top of the titanium oxide layer by means of dipping the implant in said bone-growth agent or said bone-growth-promoting agent.

* * * * *